(12) United States Patent
Harkless

(10) Patent No.: US 6,719,734 B1
(45) Date of Patent: Apr. 13, 2004

(54) ANESTHETIC DELIVERY TOOL AND METHOD OF USING

(76) Inventor: Willie E. Harkless, 1939 Saint Claude Ave., New Orleans, LA (US) 70116

(*) Notice: Subject to any disclaimer, the term of this patent is extended or adjusted under 35 U.S.C. 154(b) by 20 days.

(21) Appl. No.: 10/156,087

(22) Filed: May 28, 2002

(51) Int. Cl.[7] .......................... A61M 5/24; A61M 5/28; A61M 5/178; A61M 5/00; A61C 5/04
(52) U.S. Cl. .................... 604/201; 604/212; 604/244; 433/90
(58) Field of Search ................ 604/48, 77, 93.01, 604/173, 174, 180, 187, 195, 196, 197, 200, 201, 204, 212, 214, 244, 272; 433/80, 89, 90

(56) References Cited

U.S. PATENT DOCUMENTS

| | | | | |
|---|---|---|---|---|
| 3,964,482 A | * | 6/1976 | Gerstel et al. | 604/890.1 |
| 4,109,655 A | * | 8/1978 | Chacornac | 604/47 |
| 5,070,886 A | * | 12/1991 | Mitchen et al. | 600/584 |
| 5,201,324 A | * | 4/1993 | Swierczek | 600/583 |
| 5,636,640 A | * | 6/1997 | Staehlin | 600/577 |
| 6,132,449 A | * | 10/2000 | Lum et al. | 606/181 |
| 6,190,367 B1 | * | 2/2001 | Hall | 604/290 |
| 6,562,014 B2 | * | 5/2003 | Lin et al. | 604/317 |

* cited by examiner

Primary Examiner—Brian L. Casler
Assistant Examiner—Mark K Han

(57) ABSTRACT

A new and improved anesthetic delivery tool and method of using the tool in transmucosal absorption applications of a gel topical anesthetic agent and in subdermal injections of a liquid anesthetic agent is disclosed. The anesthetic delivery tool comprises a housing unit having a hollow central cavity with a slip plate containing a plurality of needles directed towards the front end of the housing unit. The slip plate and the front portion of the hollow central cavity defining a front-end cavity for affixing a therapeutically effective aliquot of gel topical anesthetic agent. The anesthetic delivery tool also comprises a thin membrane positioned directly behind the slip plane and a push plate positioned at the rear end of the housing unit. The push plate, the thin membrane and the rear portion of the hollow central cavity defining a rear-end cavity for affixing a therapeutically effective amount of liquid anesthetic agent. The method of using comprises obtaining, identifying, removing, adhering, aligning, allowing, positioning, exerting, removing, pulling, and discarding.

20 Claims, 4 Drawing Sheets

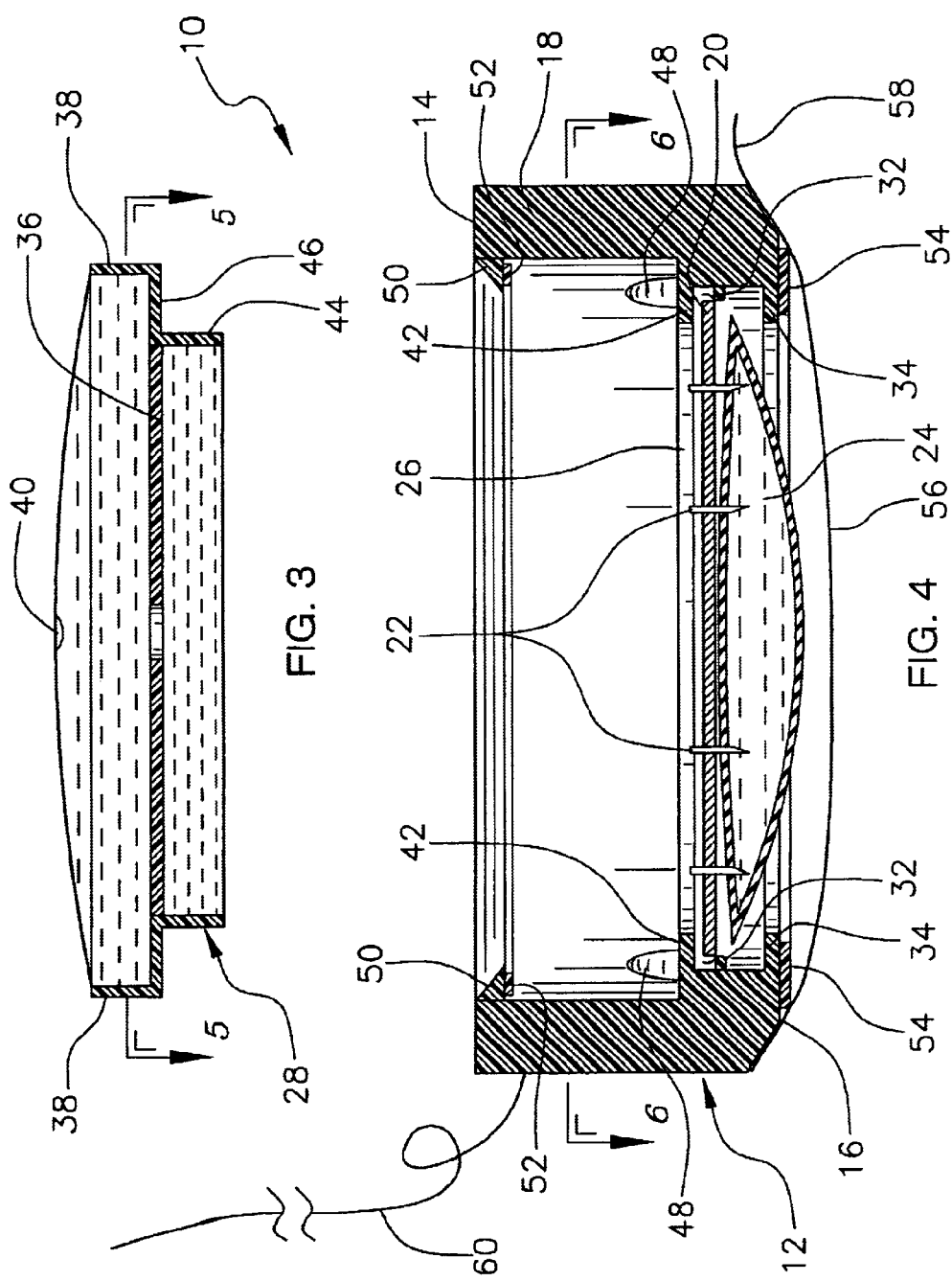

ANESTHETIC DELIVERY TOOL AND METHOD OF USING

FIELD OF THE INVENTION

The present invention relates to drug delivery devices, more particular to an anesthetic delivery tool for use in connection in performing both transmucosal absorption applications and subdermal injections of anesthetic agents.

DESCRIPTION OF THE PRIOR ART

It is generally believed and rarely argued against the consensus that pain is to avoided or at least minimized. Therefore, the application of various types of anesthetic agents to suffering patients has not only been welcomed by patients but by physicians and dentist as well. It is not generally known that physicians and dentist themselves also may suffer serious psychological deleterious effects from inflicting the inevitable pain associated with the practice of treating a suffering patient. In particular, it is has been argued that the reason why dentist suffer from unusually high suicide rates is because dentist are exposed to an environment of inflicting great pain on others. Therefore, the on-going struggle to find a means for minimizing or to eliminate pain reaches well beyond the usefulness in minimizing the pain in patients but also reaches the usefulness in minimizing the deleterious psychological effects on physicians and dentist. Presently local anesthetic delivery is achieved by transmucosal absorption of a topical anesthetic agent for topical anesthesia. This is then followed by a direct field or a nerve block to the nerves at the desired work areas desired to be anesthetized. However, as the needle penetrates the deeper layers of muscle and tissue, pain is still experienced by the patient.

A wide variety of anesthetic delivery tools is currently available on the commercial market and an even larger number of these types of devices are known in the art of anesthetic delivery tols, for example, the drug delivery device disclosed by Gerstel and Place in U.S. Pat. No. 3,964,482; the dispensing device for a liquid medicament disclosed by Thoma and Krotlinger in U.S. Pat. No. 4,781,688; the drug delivery device disclosed by Panoz in U.S. Pat. No. 4,822,617; the subdermal delivery device disclosed by Kriesel et all in U.S. Pat. No. 5,693,018; the intradermal drug delivery device and method for intradermal delivery of drugs disclosed by Gross and Kelly in U.S. Pat. No. 5,848,991; and the fluid delivery device with collapsible needle cover disclosed by Kriesel and Thompson in U.S. Pat. No. 6,126,637.

While all of the above-described devices fulfill their respective, particular objectives and requirements, the aforementioned patents do not describe an anesthetic delivery tool having a housing unit with a hollow central cavity, a slip plate containing a plurality of needles and a push plate, wherein the slip plate is slidably attached within the hollow central cavity. These elements would specifically match the user's particular individual needs of making it possible to have a front-end cavity containing a gel topical anesthetic agent for use in transmucosal absorption applications, as well as, a rear-end cavity containing a liquid anesthetic agent for use in subdermal injections of the liquid anesthetic agent. The above-described patents make no provision for a device capable of applying anesthetic agents via transmucosal absorption applications followed by subdermal injections.

Therefore, a need exists for a new and improved anesthetic delivery tool having a housing unit with a hollow central cavity, a slip plate containing a plurality of needles and a push plate, wherein the slip plate is slidably attached within the hollow central cavity. In this respect, the anesthetic delivery tool according to the present invention substantially departs from the conventional concepts and designs of the prior art, and in doing so provides an apparatus primarily developed for the purpose of making it possible to have a front-end cavity containing a gel topical anesthetic agent for use in transmucosal absorption applications, as well as, a rear-end cavity containing a liquid anesthetic agent for use in subdermal injections of the liquid anesthetic agent.

SUMMARY OF THE INVENTION

The present device, according to the principles of the present invention, overcomes the shortcomings of the prior art by providing a new and improved anesthetic delivery tool and method of using the tool in transmucosal absorption applications of a gel topical anesthetic agent and in subdermal injections of a liquid anesthetic agent is disclosed. The anesthetic delivery tool comprises a housing unit having a hollow central cavity with a slip plate containing a plurality of needles directed towards the front end of the housing unit. The slip plate and the front portion of the hollow central cavity define a front-end cavity for affixing a therapeutically effective aliquot of gel topical anesthetic agent. The anesthetic delivery tool also comprises a thin membrane positioned directly behind the slip plane and a push plate positioned at the rear end of the housing unit. The push plate, the thin membrane and the rear portion of the hollow central cavity defining a rear-end cavity for affixing a therapeutically effective amount of liquid anesthetic agent.

In view of the foregoing disadvantages inherent in the known type anesthetic delivery tools now present in the prior art, the present invention provides an improved anesthetic delivery tool, which will be described subsequently in great detail, is to provide a new and improved anesthetic delivery tool which is not anticipated, rendered obvious, suggested, or even implied by the prior art, either alone or in any combination thereof.

To attain this, the present invention essentially comprises a housing unit having a hollow central cavity with a slip plate containing a plurality of needles directed towards the front end of the housing unit. The slip plate and the front portion of the hollow central cavity define a front-end cavity for affixing a therapeutically effective aliquot of gel topical anesthetic agent. The anesthetic delivery tool also comprises a thin membrane positioned directly behind the slip plane and a push plate positioned at the rear end of the housing unit. The push plate, the thin membrane and the rear portion of the hollow central cavity defining a rear-end cavity for affixing a therapeutically effective amount of liquid anesthetic agent.

There has thus been outlined, rather broadly, the more important features of the invention in order that the detailed description thereof that follows may be better understood, and in order that the present contribution of the art may be better appreciated.

The invention may also include a gingival adhesive pad, a detachable film cover and a safety string. There are of course, additional features of the invention that will be described hereinafter and which will form the subject matter of the claims attached.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be used as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved anesthetic delivery tool that has all the advantages of the prior art anesthetic delivery tool and none of the disadvantages.

It is another object of the present invention to provide a new and improved anesthetic delivery tool that may be easily and efficiently manufactured and marketed.

An even further object of the present invention is to provide a new and improved anesthetic delivery tool that has a low cost of manufacture with regard to both materials and labor, and which accordingly is then susceptible of low prices of sale to the consuming public, thereby making such multipurpose storage unit and system economically available to the buying public.

Still another object of the present invention is to provide a new anesthetic delivery tool that provides in the apparatuses and methods of the prior art some of the advantages thereof, while simultaneously overcoming some of the disadvantages normally associated therewith.

Even still another object of the present invention is to provide a anesthetic delivery tool having a housing unit with a hollow central cavity, a slip plate containing a plurality of needles and a push plate, wherein the slip plate is slidably attached within the hollow central cavity. This makes it possible to have a front-end cavity containing a gel topical anesthetic agent for use in transmucosal absorption applications, as well as, a rear-end cavity containing a liquid anesthetic agent for use in subdermal injections of the liquid anesthetic agent.

Lastly, it is an object of the present invention to provide a new and improved method of using the present invention comprises obtaining, identifying, removing, adhering, aligning, allowing, positioning, exerting, removing, pulling, discarding.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompany drawings and description matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross sectional side view of a push plate of a preferred embodiment of the anesthetic delivery tool of the present invention;

FIG. 4 is a cross sectional side view of a housing unit of a preferred embodiment of the anesthetic delivery tool of the present invention;

The same reference numerals refer to the same parts throughout the various figures.

DETAILED DESCRIPTION OF THE PREFERRED EMBODIMENT

Figure 1:
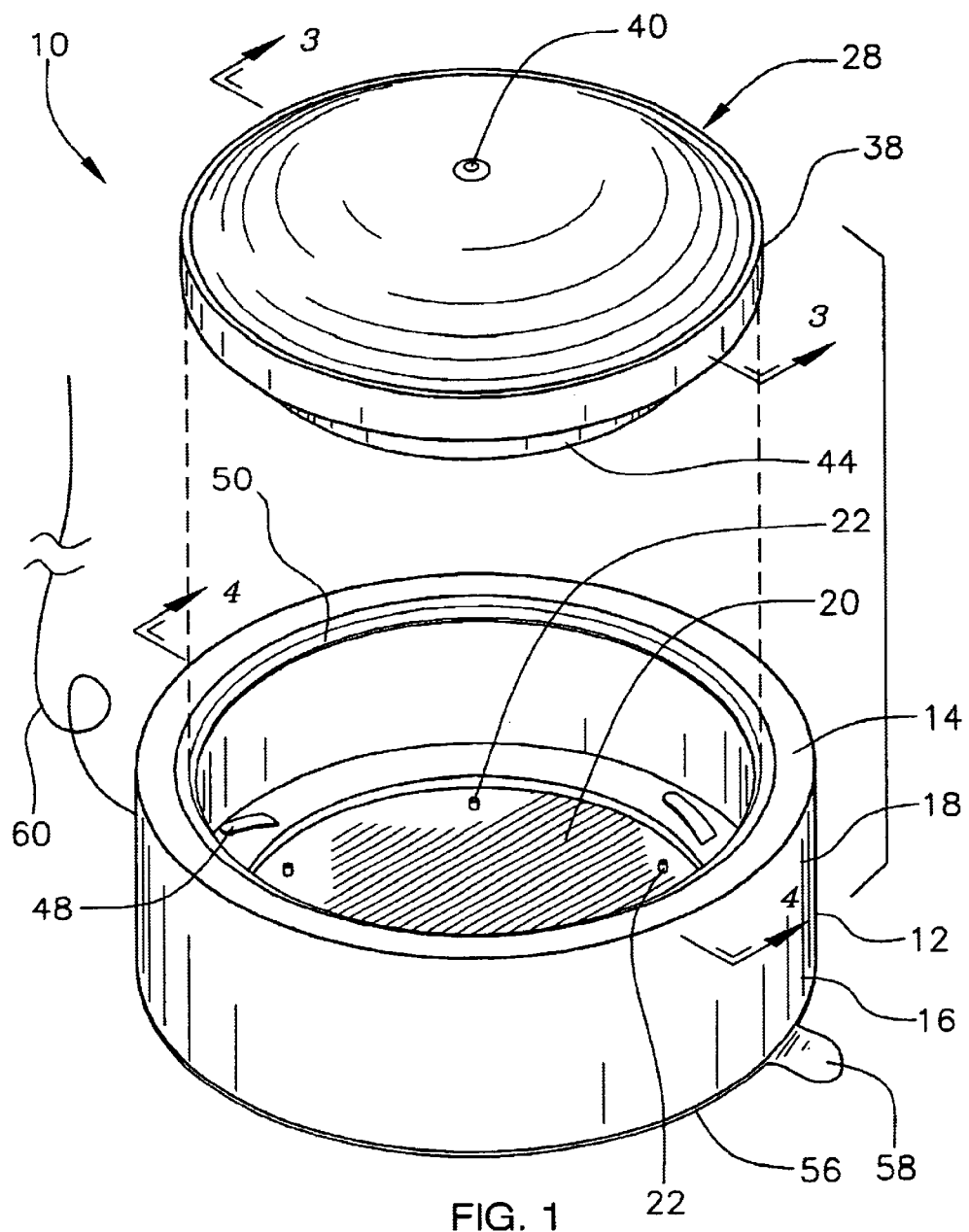
FIG. 1 is a perspective rear view of a preferred embodiment of the anesthetic delivery tool constructed in accordance with the principles of the present invention.

Referring now to the drawings, and in particular FIGS. 1 to 6 thereof, one preferred embodiment of the present invention is shown and generally designated by the reference numeral 10. One embodiment of the anesthetic delivery tool 10 for use in a transmucosal absorption application of a gel topical anesthetic agent and for use in a subdermal injection of a liquid anesthetic agent, the anesthetic delivery tool 10 comprises a housing unit 12, a slip plate 20, a plurality of hollow needles 22, a first aliquot 24 of the gel topical anesthetic agent, a thin membrane 26, a push plate 28, and an second aliquot of a liquid anesthetic agent. The housing unit 12 comprises rear end 14, a front end 16 and a continuous wall 18 defining a hollow central cavity with a rear orifice and a front orifice. The slip plate 20 comprises a front surface, a rear surface and an edge, in which the edge of the slip plate 20 is slidably attached around a first portion of the interior surface of the continuous wall 18 of the housing unit 12. The part of the central cavity between the front surface of the slip plate 20 and the front end 16 of the housing unit 12 define a front-end cavity. When a forward bearing force is exerted onto the rear surface of the slip plate 20 the slip plate 20 is capable of sliding forward into a portion of the front-end cavity. The plurality of hollow needles 22 is attached longitudinally through the slip plate 20, in which the sharp-ends of the needles 22 extend away from the front surface of the slip plate 20 into the front-end cavity and generally pointing towards the front end 16 of the housing. The butt-ends of the needles 22 extend away from the rear surface of the slip plate 20 and generally point towards the rear end 14 of the housing. When the forward bearing force is exerted onto the rear surface of the slip plate 20 then the slip plate 20 is capable of sliding forward into a portion of the front-end cavity whereby extending the sharp-ends of the needles 22 beyond the front-end cavity. The first aliquot 24 of the gel topical anesthetic agent is affixed onto the front-end cavity, in which the first aliquot 24 of the gel topical anesthetic agent covers a portion of the sharp-ends of the needles 22. The thin membrane 26 comprises a rear surface, a front surface and an edge, in which the edge of the thin membrane 26 is continuously attached around a second portion of the interior surface of the continuous wall 18 of the housing unit 12. The thin membrane 26 is positioned behind the slip plate 20, so that the thin membrane 26 penetrateable with the butt-ends of the needles 22 when the forward bearing force is exerted onto the rear surface of the thin membrane 26. The push plate 28 comprises a exterior surface, an interior surface and an edge, the edge of the push plate 28 is attached around the rear end 14 of the housing, wherein the part of the central cavity between the thin membrane 26 and the push plate 28 defining a rear-end cavity 30. The second aliquot of the liquid anesthetic agent is affixed within the rear-end cavity 30.

Another embodiment of the anesthetic delivery tool 10 comprises: a housing unit 12, a slip plate 20, a plurality of hollow needles 22, an first aliquot 24, a thin membrane 26, a push plate 28, a finger protector sheet 36, a septum cap 40, a spring 48, an second aliquot, an adhesive strip 52, a gingival adhesive pad 54, a detachable film cover 56, and a string 60. The housing unit 12 has rear end 14, a front end 16 and a continuous wall 18 defining a hollow central cavity with a rear orifice and a front orifice. The continuous wall 18 of the housing unit 12 including: a ridge 32, a lip 34, a ledge 42, and a rim 50. The ridge 32 inwardly extends at a first portion of the interior surface of the continuous wall 18. The lip 34 inwardly extends at the front end 16 of the housing within the central cavity. The ledge 42 inwardly extends along a second portion of the interior surface, the ledge 42 defining an orifice having a width. The rim 50 is attached to the rear end 14 of the housing unit 12, in which the rim 50 defining an aperture having a width. The slip plate 20 has a front surface, a rear surface and an edge, the edge of the slip plate 20 is slidably attached around the first portion of the interior surface of the continuous wall 18 of the housing unit 12. The edge of the slip plate 20 is attached to the ridge 32. The part of the central cavity between the front surface of the slip plate 20 and the front end 16 of the housing unit 12 define a front-end cavity. When a forward bearing force is exerted onto the rear surface of the slip plate 20 the slip plate 20 is capable of sliding forward into a portion of the front-end cavity. The lip 34 has a width greater than the width of the slip plate 20, wherein when the forward bearing force is exerted onto the rear surface of the slip plate 20, the slip plate 20 is capable of sliding forward into a portion of the front-end cavity and the slip plate 20 is not capable of sliding past the lip 34. Whereby the slip plate 20 is retainable within the front-end cavity of the housing by the lip 34. The plurality of hollow needles 22 is attached longitudinally through the slip plate 20. The sharp-ends of the needles 22 extend away from the front surface of the slip plate 20 into the front-end cavity and generally point towards the front end 16 of the housing. The butt-ends of the needles 22 extend away from the rear surface of the slip plate 20 and generally point towards the rear end 14 of the housing. When the forward bearing force is exerted onto the rear surface of the slip plate 20 then the slip plate 20 is capable of sliding forward into a portion of the front-end cavity whereby extending the sharp-ends of the needles 22 beyond the front-end cavity. The first aliquot 24 of the gel topical anesthetic agent is affixed onto the front-end cavity, wherein the aliquot of the gel topical anesthetic agent covers a portion of the sharp-ends of the needles 22. The thin membrane 26 has a rear surface, a front surface and an edge. The edge of the thin membrane 26 is continuously attached around the ledge 42 at the second portion of the interior surface of the continuous wall 18 of the housing unit 12. The thin membrane 26 is positioned behind the slip plate 20. The thin membrane 26 is penetrateable with the butt-ends of the needles 22 when the forward bearing force is exerted onto the rear surface of the thin membrane 26. The push plate 28 has a exterior surface, an interior surface and an edge. The edge of the push plate 28 is attached around the rear end 14 of the housing. The part of the central cavity between the thin membrane 26 and the push plate 28 defining a rear-end cavity 30. The edge of the push plate 28 comprises a sleeve 38 and a neck 44. The sleeve 38 has a exterior width slightly smaller than the width of the central cavity of the housing, so that the sleeve 38 is slidably attached with the inner surface of the continuous wall 18 of the housing unit 12 within the rear-end cavity 30. The sleeve 38 has an outside surface and an inside surface, in which the inside surface has an interior width. The inside surface of the sleeve 38 and the interior surface of the push plate 28 define a hollow shaft. The hollow shaft is in fluid communications with the rear-end cavity 30. The neck 44 is attached to the sleeve 38 of the push plate 28. The neck 44 has a width less than the sleeve 38, so that the neck 44 and the sleeve 38 defining a shoulder 46. When the forward bearing force is exerted on the exterior surface of the push plate 28, then the push plate 28 is capable of sliding forwardly along the inner surface of the continuous wall 18 of the housing unit 12 and the shoulder 46 of the push plate 28 is not capable of sliding past the ledge 42. Whereby the ledge 42 is capable of preventing the push plate 28 from sliding outside of the rear-end cavity 30. The orifice of the ledge 42 has a width less than the external width of the sleeve 38. When the forward bearing force is exerted on the exterior surface of the push plate 28, then the push plate 28 is capable of sliding forwardly along the inner surface of the continuous wall 18 of the housing unit 12 and the push plate 28 is not capable of sliding past the ledge 42. Whereby the ledge 42 is capable of preventing the push plate 28 from sliding outside of the rear-end cavity 30. The aperture of the rim 50 has a width less than the external width of the sleeve 38 of the push plate 28, in which the push plate 28 is restrained within the central cavity by the rim 50. The finger protector sheet 36 has a rear surface, a front surface, a hole and an edge. The edge of the finger protector sheet 36 bisects the hollow shaft of the push plate 28 by being attached around a portion of the interior surface of the sleeve 38. The part of the hollow shaft between the finger protector sheet 36 and the interior surface of the push plate 28 defining a top zone of the hollow shaft. The part of the hollow shaft between the finger protection sheet and the remaining part of the hollow shaft defines a bottom zone of the hollow shaft. The top zone is in fluid communications with the bottom zone through the hole in the finger protector sheet 36. The finger protector sheet 36 is made of a puncture resistant material resistant to being penetrated by the butt-ends of the needles 22. The septum cap 40 is attached to the push plate 28. The spring 48 is attached to ledge 42, so that when the forward bearing force is exerted on the exterior surface of the push plate 28, then the push plate 28 is capable of sliding forwardly along the inner surface of the continuous wall 18 of the housing unit 12. The spring 48 is capable of contacting the push plate 28, in which the spring 48 provides a resistance against the forward bearing force when the push plate 28 slides towards the ledge 42. The second aliquot of the liquid anesthetic agent is affixed within the rear-end cavity 30. The adhesive strip 52 is attached to the rim 50 and is detachably attached to a portion of the exterior surface of the push plate 28. When the forward bearing force is exerted onto the push plate 28, then the adhesive pad is capable of detaching from the push plate 28. The adhesive strip 52 maintains the push plate 28 against the rim 50 until the forward bearing force is exerted onto the push plate 28. The gingival adhesive pad 54 is attached to the front end 16 of the housing unit 12. The gingival adhesive pad 54 is intended to temporarily attach the housing unit 12 onto a patient's gingival work area. The detachable film cover 56 is attached onto the front end 16 of the housing unit 12. The film cover 56 maintains in place the gel topical anesthetic agent within the front-end cavity. The film cover 56 has a pull tab 58. Finally, the string 60 is attached to the housing.

One preferred method of using an anesthetic delivery tool 10 for use in a transmucosal absorption application of a gel topical anesthetic agent and for use in a subdermal injection of a liquid anesthetic agent, the method comprising the steps of obtaining, identifying, removing, adhering, aligning, allowing, positioning, exerting, removing, pulling, discarding. The obtaining step comprisesobtaining the anesthetic delivery tool 10 comprising: a housing unit 12 having rear end 14, a front end 16 and a continuous wall 18 defining a hollow central cavity with a rear orifice and a front orifice, wherein the continuous wall 18 of the housing unit 12 including: a ridge 32 inwardly extending at a first portion of the interior surface of the continuous wall 18; a lip 34 inwardly extending at the front end 16 of the housing within the central cavity; a ledge 42 inwardly extending along a second portion of the interior surface, the ledge 42 defining an orifice having a width; and a rim 50 attached to the rear end 14 of the housing unit 12, the rim 50 defining an aperture having a width; a slip plate 20 having a front surface, a rear surface and an edge, the edge of the slip plate 20 slidably attached around the first portion of the interior surface of the continuous wall 18 of the housing unit 12, the edge of the slip plate 20 is attached to the ridge 32, the part of the central cavity between the front surface of the slip plate 20 and the front end 16 of the housing unit 12 defining a front-end cavity, wherein when a forward bearing force is exerted onto the rear surface of the slip plate 20 the slip plate 20 is capable of sliding forward into a portion of the front-end cavity, the lip 34 having a width greater than the width of the slip plate 20, wherein when the forward bearing force is exerted onto the rear surface of the slip plate 20, the slip plate 20 is capable of sliding forward into a portion of the front-end cavity and the slip plate 20 is not capable of sliding past the lip 34, whereby the slip plate 20 is retainable within the front-end cavity of the housing; a plurality of hollow needles 22 attached longitudinally through the slip plate 20, wherein the sharp-ends of the needles 22 extending away from the front surface of the slip plate 20 into the front-end cavity and generally pointing towards the front end 16 of the housing, wherein the butt-ends of the needles 22 extending away from the rear surface of the slip plate 20 and generally pointing towards the rear end 14 of the housing, wherein when the forward bearing force is exerted onto the rear surface of the slip plate 20 the slip plate 20 is capable of sliding forward into a portion of the front-end cavity whereby extending the sharp-ends of the needles 22 beyond the front-end cavity; an first aliquot 24 of the gel topical anesthetic agent affixed onto the front-end cavity, wherein the first aliquot 24 of the gel topical anesthetic agent covering a portion of the sharp-ends of the needles 22; a thin membrane 26 having a rear surface, a front surface and an edge, the edge of the thin membrane 26 continuously attached around the ledge 42 at the second portion of the interior surface of the continuous wall 18 of the housing unit 12, the thin membrane 26 positioned behind the slip plate 20, the thin membrane 26 penetrateable with the butt-ends of the needles 22 when the forward bearing force is exerted onto the rear surface of the thin membrane 26; a push plate 28 having a exterior surface, an interior surface and an edge, the edge of the push plate 28 attached around the rear end 14 of the housing, wherein the part of the central cavity between the thin membrane 26 and the push plate 28 defining a rear-end cavity 30, the edge of the push plate 28 comprises a sleeve 38 and a neck 44, the sleeve 38 having a exterior width slightly smaller than the width of the central cavity of the housing, the sleeve 38 slidably attached with the inner surface of the continuous wall 18 of the housing unit 12 within the rear-end cavity 30, the sleeve 38 having an outside surface and an inside surface, the inside surface having an interior width, wherein the inside surface of the sleeve 38 and the interior surface of the push plate 28 defining a hollow shaft, the hollow shaft in fluid communications with the rear-end cavity 30, the a neck 44 attached to the sleeve 38 of the push plate 28, the neck 44 having a width less than the sleeve 38, the neck 44 and the sleeve 38 defining a shoulder 46, wherein when the forward bearing force is exerted on the exterior surface of the push plate 28, the push plate 28 is capable of sliding forwardly along the inner surface of the continuous wall 18 of the housing unit 12 and the shoulder 46 of the push plate 28 is not capable of sliding past the ledge 42, whereby the ledge 42 is capable of preventing the push plate 28 from sliding outside of the rear-end cavity 30, the orifice of the ledge 42 having a width less than the external width of the sleeve 38, wherein when the forward bearing force is exerted on the exterior surface of the push plate 28, then the push plate 28 is capable of sliding forwardly along the inner surface of the continuous wall 18 of the housing unit 12 and the push plate 28 is not capable of sliding past the ledge 42, whereby the ledge 42 is capable of preventing the push plate 28 from sliding outside of the rear-end cavity 30, the aperture of the rim 50 having a width less than the external width of the sleeve 38 of the push plate 28, whereby the push plate 28 is restrained within the central cavity by the rim 50; a finger protector sheet 36 having a rear surface, a front surface, a hole and an edge, the edge of the finger protector sheet 36 bisecting the hollow shaft of the push plate 28 by being attached around a portion of the interior surface of the sleeve 38 wherein the part of the hollow shaft between the finger protector sheet 36 and the interior surface of the push plate 28 defining a top zone of the hollow shaft, and the part of the hollow shaft between the finger protection sheet and the remaining part of the hollow shaft defining a bottom zone of the hollow shaft, the top zone in fluid communications with the bottom zone through the hole in the finger protector sheet 36, wherein the finger protector sheet 36 is made of a puncture resistant material resistant to being penetrated by the butt-ends of the needles 22; a septum cap 40 attached to the push plate 28; a spring 48 attached to ledge 42, wherein when the forward bearing force is exerted on the exterior surface of the push plate 28, the push plate 28 is capable of sliding forwardly along the inner surface of the continuous wall 18 of the housing unit 12 and the spring 48 is capable of contacting the push plate 28, whereby the spring 48 providing resistance against the forward bearing force when the push plate 28 slides towards the ledge 42; an second aliquot of the liquid anesthetic agent affixed within the rear-end cavity 30; an adhesive strip 52 attached to the rim 50 and detachably attached to a portion of the exterior surface of the push plate 28, wherein when the forward bearing force is exerted onto the push plate 28, the adhesive pad is capable of detaching from the push plate 28, whereby the adhesive strip 52 maintaining the push plate 28 against the rim 50 until the forward bearing force is exerted onto the push plate 28; a gingival adhesive pad 54 attached to the front end 16 of the housing unit 12, the gingival adhesive pad 54 intended to temporarily attach the housing unit 12 onto a patient's gingival work area; a detachable film cover 56 attached onto the front end 16 of the housing unit 12, the film cover 56 maintaining in place the gel topical anesthetic agent within the front-end cavity, the film cover 56 having a pull tab 58; and a string 60 attached to the housing. The identifying step comprises identifying the gingival work area in the patient's mouth. The removing step comprises removing the detachable film cover 56 from the front end 16 of the housing unit 12. The adhering step comprises adhering the front end 16 of the housing unit 12 to the gingival work area in the patient's mouth. The aligning step comprises aligning the string 60 outside of the patient's mouth. The allowing step comprises allowing time to pass so that the gel topical anesthetic agent can be transmucosally absorbed in the gingival work area in the patient's mouth. The positioning step comprises positioning a finger over the exterior surface of the push plate 28. The exerting step comprises exerting the forward bearing force onto the exterior surface of the push plate 28 so that the slip plate 20 slides forward and the sharp-ends of the needles 22 puncture the gingival work area in the patient's mouth as well as penetrate the thin membrane 26 and subsequently inject the liquid anesthetic agent into the surrounding tissue of the gingival work area in the patient's mouth. The removing step comprises removing the finger from the exterior surface of the push plate 28. The pulling step comprises pulling the housing unit 12 out of the patient's mouth. The discarding step comprises discarding the used housing unit 12.

The push plate 28 may comprise any number of different devices as long as the push plate can be used to squeeze the liquid anesthetic agent from the confines of the rear-end cavity 30 through the plurality of needles 22. One preferred configuration of the push plate comprises a flexible membrane attached around the rear orifice of the housing, wherein when the rear-end cavity 30 is filled with liquid anesthetic agent, the push plate 28 is capable of bulging outwardly from the rear-end of the housing and when the forward bearing force is exerted onto the exterior surface of the push plate 28, then the flexible member is capable of bulging inwardly from the rear-end of the housing into a portion of the rear-end cavity 30, whereby reducing the volume in the rear-end cavity 30. Another preferred configuration of the push plate 28 is that it comprises a sleeve 38 having a exterior width slightly smaller than the width of the central cavity of the housing, the sleeve 38 is slidably attached with the inner surface of the continuous wall 18 of the housing unit 12 within the rear-end cavity 30, wherein when the forward bearing force is exerted on the exterior surface of the push plate 28, then the push plate 28 is capable of sliding forwardly along the inner surface of the continuous wall 18 of the housing unit 12 whereby reducing the volume of the rear-end cavity 30. The sleeve 38 may further comprise an outside surface and an inside surface, the inside surface has an interior width, wherein the inside surface of the sleeve 38 and the interior surface of the push plate 28 defining a hollow shaft, the hollow shaft in fluid communications with the rear-end cavity 30. Yet another preferred configuration of the push plate 28 is that it further comprises a septum cap 40 is attached to the push plate 28, wherein the septum cap 40 intended for allowing the aliquot of liquid anesthetic agent to volumetrically affixed within the rear-end cavity 30. The septum cap 40 is intended as the route of injecting the liquid anesthetic into the rear-end cavity. Still yet another preferred configuration of the push plate 28 is that it further comprises a neck 44 attached to the sleeve 38 of the push plate 28, the neck 44 has a width less than the sleeve 38, the neck 44 and the sleeve 38 defining a shoulder 46, wherein when the forward bearing force is exerted on the exterior surface of the push plate 28, the the push plate 28 is capable of sliding forwardly along the inner surface of the continuous wall 18 of the housing unit 12 and the shoulder 46 of the push plate 28 is not capable of sliding past the ledge 42, whereby the ledge 42 is capable of preventing the push plate 28 from sliding outside of the rear-end cavity 30.

The first portion of the interior surface of the continuous wall 18 of the housing unit 12 may optionally comprise an inwardly extending ridge 32. The edge of the slip plate 20 is attached to the ridge 32, wherein when the forward bearing force is exerted onto the rear surface of the slip plate 20 the attachment of the ridge 32 to the edge of the slip plate 20 is breakable, whereby the slip plate 20 is capable of sliding forward into a portion of the front-end cavity whereby extending the sharp-ends of the needles 22 beyond the front-end cavity.

The first portion of the interior surface of the continuous wall 18 of the housing unit 12 may also optionally comprise an inwardly extending lip 34. The lip 34 positioned near the front end 16 of the housing within the central cavity, the lip 34 has a width greater than the width of the slip plate 20, wherein when the forward bearing force is exerted onto the rear surface of the slip plate 20, the slip plate 20 is capable of sliding forward into a portion of the front-end cavity and the slip plate 20 is not capable of sliding past the lip 34, whereby the slip plate 20 is retainable within the front-end cavity of the housing.

An optional finger protector sheet 36 may be added to the anesthetic delivery tool 10. The finger protector sheet 36 comprises rear surface, a front surface, a hole and an edge. The finger protector sheet may comprise any number of different types of sheets as long as the finger protector sheet functions by protecting the finger pushing on the exterior surface of the push plate 28 from being jabbed by the butt-ends of the plurality of needles 22. One preferred configuration of the finger protector sheet 36 comprises that the finger protector sheet 36 is attached around a portion of the interior surface of the continuous wall 18 of the housing unit 12 the rear-end cavity 30, wherein the finger protector sheet 36 bisects the rear-end cavity 30, the part of the rear-end cavity 30 between the finger protector sheet 36 and the push plate 28 defining a top chamber of the rear-end cavity 30, and the part of the rear-end cavity 30 between the finger protection sheet and the thin membrane 26 defining a bottom chamber of the rear-end cavity 30, the top chamber in fluid communications with the bottom chamber through the hole in the finger protector sheet 36, wherein the finger protector sheet 36 is made of a puncture resistant material resistant to being penetrated by the butt-ends of the needles 22. Another preferred configuration of the finger protector sheet is that it is a component of the push plate 28 in which the finger protector sheet 36 has a rear surface, a front surface, a hole and an edge, the edge of the finger protector sheet 36 bisecting the hollow shaft by being attached around a portion of the interior surface of the sleeve 38 wherein the part of the hollow shaft between the finger protector sheet 36 and the interior surface of the push plate 28 defining a top zone of the hollow shaft, and the part of the hollow shaft between the finger protection sheet and the remaining part of the hollow shaft defining a bottom zone of the hollow shaft, the top zone in fluid communications with the bottom zone through the hole in the finger protector sheet 36, wherein the finger protector sheet 36 is made of a puncture resistant material resistant to being penetrated by the butt-ends of the needles 22.

An optional ledge 42 extending inwardly from the interior surface of said continuous wall of said housing may be added to anesthetic delivery tool 10. The ledge 42 defining an orifice where the thin membrane 26 is attached, wherein the orifice of the ledge 42 has a width less than the external width of the sleeve 38, wherein when the forward bearing force is exerted on the exterior surface of the push plate 28, then the push plate 28 is capable of sliding forwardly along the inner surface of the continuous wall 18 of the housing unit 12 and the push plate 28 is not capable of sliding past the ledge 42, whereby the ledge 42 is capable of preventing the push plate 28 from sliding outside of the rear-end cavity 30.

An optional spring 48 may be added to the anesthetic delivery tool 10. The spring 48 may be attached to the optional ledge 42, wherein when the forward bearing force is exerted on the exterior surface of the push plate 28, the push plate 28 is capable of sliding forwardly along the inner surface of the continuous wall 18 of the housing unit 12 and the spring 48 is capable of contacting the push plate 28, whereby the spring 48 providing resistance against the forward bearing force when the push plate 28 slides towards the ledge 42.

An optional rim 50 may be attached to the anesthetic delivery tool 10. The rim 50 is attached to the rear end 14 of the housing unit 12, the rim 50 defining an aperture that has a width less than the external width of the sleeve 38 of the push plate 28, wherein the push plate 28 is restrained within the central cavity by the rim 50.

An optional adhesive strip 52 may be added to the anesthetic delivery tool 10. The adhesive strip 52 is attached to the rim 50 and is detachably attached to a portion of the exterior surface of the push plate 28, wherein when the forward bearing force is exerted onto the push plate 28, the adhesive pad is capable of detaching from the push plate 28, whereby the adhesive strip 52 maintaining the push plate 28 against the rim 50 until the forward bearing force is exerted onto the push plate 28.

An optional gingival adhesive pad 54 may be added to the anesthetic delivery tool 10. The gingival adhesive pad 54 is attached to the front end 16 of the housing unit 12. The gingival adhesive pad 54 intended to temporarily attach the housing unit 12 onto a patient's gingival work area.

An optional detachable film cover 56 may be added to the anesthetic delivery tool 10. The detachable film cover 56 is attached onto the front end 16 of the housing unit 12. The film cover 56 maintaining in place the gel topical anesthetic agent within the front-end cavity. The film cover 56 may have a pull tab 58 for providing a convenient grip for easy removal of the film cover 56 over the front end 16 of the housing unit 12.

An optional string 60 may be added to 18. The anesthetic delivery tool 10 described in claim 1 further comprising a string 60 attached to the housing, the string 60 intended to be used as a safety device to retrieve the housing from a patient's mouth or esophagus.

Figure 2:
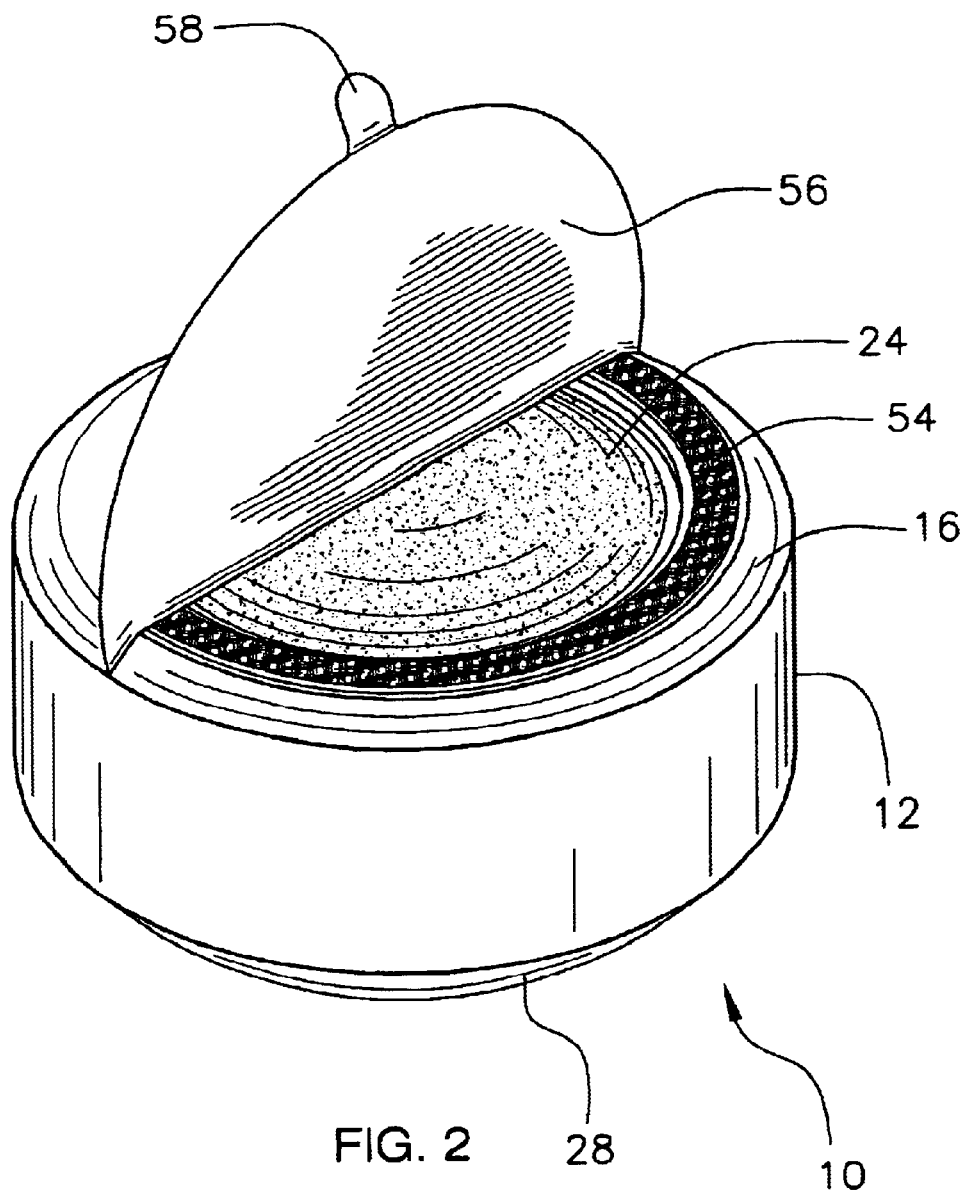
FIG. 2 is a perspective forward view of a preferred embodiment of the anesthetic delivery tool of the present invention.

FIG. 1 and FIG. 2 depict perspective rear and forward views of a preferred embodiment of the anesthetic delivery tool 10. The anesthetic delivery tool is shown having a housing unit 12, a slip plate 20, a plurality of hollow needles 22, a first aliquot 24 of the gel topical anesthetic agent, a push plate 28, and a rear-end cavity 30. The housing unit 12 comprises a rear end 14, a front end 16 and a continuous wall 18 defining a hollow central cavity with a rear orifice and a front orifice. The slip plate 20 comprises a front surface, a rear surface and an edge, in which the edge of the slip plate 20 is slidably attached around a first portion of the interior surface of the continuous wall 18 of the housing unit 12. The part of the central cavity between the front surface of the slip plate 20 and the front end 16 of the housing unit 12 defining a front-end cavity where the first aliquot 24 of the gel topical anaesthesia is affixed. The plurality of hollow needles 22 is attached longitudinally through the slip plate 20, in which the butt-ends of the needles 22 are shown extending away from the rear surface of the slip plate 20 and generally pointing towards the rear end 14 of the housing. The first aliquot 24 of the gel topical anesthetic agent is affixed onto the front-end cavity, in which the first aliquot 24 of the gel topical anesthetic agent covers a portion of the sharp-ends of the needles 22. The thin membrane 26 (not shown) comprises a rear surface, a front surface and an edge, in which the edge of the thin membrane 26 is continuously attached around a second portion of the interior surface of the continuous wall 18 of the housing unit 12. The thin membrane 26 is positioned behind the slip plate 20, so that the thin membrane 26 can be penetrated with the butt-ends of the needles 22 when the forward bearing force is exerted onto the rear surface of the thin membrane 26. The push plate 28 comprises a exterior surface, an interior surface and an edge, the edge of the push plate 28 is attached around the rear end 14 of the housing. The part of the central cavity between the thin membrane 26 and the push plate 28 defining a rear-end cavity 30, in which the second aliquot of the liquid anesthetic agent is affixed.

FIG. 3 and FIG. 4 depict cross sectional side views of a push plate 28 and the housing unit 12 of a preferred embodiment of the anesthetic delivery tool 10 of the present invention. The dental anesthetic delivery device 10 comprises a housing unit 12, a slip plate 20, a plurality of hollow needles 22, an first aliquot 24, a thin membrane 26, a push plate 28, a finger protector sheet 36, a septum cap 40, a spring 48, an second aliquot, an adhesive strip 52, a gingival adhesive pad 54, a detachable film cover 56, and a string 60. The housing unit 12 comprises rear end 14, a front end 16 and a continuous wall 18 defining a hollow central cavity with a rear orifice and a front orifice. The continuous wall 18 of the housing unit 12 is shown having a ridge 32, a lip 34, a ledge 42, and a rim 50. The ridge 32 inwardly extends at a first portion of the interior surface of the continuous wall 18. The lip 34 inwardly extends at the front end 16 of the housing within the central cavity. The ledge 42 inwardly extends along a second portion of the interior surface, the ledge 42 defining an orifice having a width. The rim 50 is attached to the rear end 14 of the housing unit 12, in which the rim 50 defining an aperture having a width. The slip plate 20 comprises a front surface, a rear surface and an edge, in which the edge of the slip plate 20 is slidably attached around a first portion of the interior surface of the continuous wall 18 of the housing unit 12. The edge of the slip plate 20 is attached to the ridge 32. The part of the central cavity between the front surface of the slip plate 20 and the front end 16 of the housing unit 12 define a front-end cavity. The first aliquot 24 of the gel topical anesthetic agent is affixed onto the front-end cavity, wherein the aliquot of the gel topical anesthetic agent covers a substantial portion of the sharp-ends of the needles 22. The gingival adhesive pad 54 is attached to the front end 16 of the housing unit 12. The gingival adhesive pad 54 is intended to temporarily attach the housing unit 12 onto a patient's gingival work area. The detachable film cover 56 is attached onto the front end 16 of the housing unit 12. The film cover 56 maintains in place the gel topical anesthetic agent within the front-end cavity. The film cover 56 is shown having a pull tab 58. The string 60 is attached to the housing, in which the string 60 is intended to be used as a retrieval safety device for convenient and safe removal of the anesthetic delivery tool 10 from a work area, such as, a patient's mouth or esophagus. When a forward bearing force is exerted onto the rear surface of the slip plate 20 the slip plate 20 is capable of sliding forward into a portion of the front-end cavity. The lip 34 is intended to have a width greater than the width of the slip plate 20, so that the slip plate 20 is not capable of sliding past the lip 34. The plurality of hollow needles 22 is attached longitudinally through the slip plate 20. The sharp-ends of the needles 22 extend away from the front surface of the slip plate 20 into the front-end cavity and generally point towards the front end 16 of the housing. The butt-ends of the needles 22 extend away from the rear surface of the slip plate 20 and generally point towards the rear end 14 of the housing. When the forward bearing force is exerted onto the rear surface of the slip plate 20 then the slip plate 20 is capable of sliding forward into a portion of the front-end cavity whereby extending the sharp-ends of the needles 22 beyond the front-end cavity and into the subdermal layer of the patient. The thin membrane 26 has a rear surface, a front surface and an edge. The edge of the thin membrane 26 is continuously attached around the ledge 42 at the second portion of the interior surface of the continuous wall 18 of the housing unit 12. The thin membrane 26 is positioned behind the slip plate 20. The thin membrane 26 is penetrateable with the butt-ends of the needles 22 when the forward bearing force is exerted onto the rear surface of the thin membrane 26. The push plate 28 has a exterior surface, an interior surface and an edge. The edge of the push plate 28 is attached around the rear end 14 of the housing. The part of the central cavity between the thin membrane 26 and the push plate 28 defining a rear-end cavity 30. The edge of the push plate 28 comprises a sleeve 38 and a neck 44. The sleeve 38 has a exterior width slightly smaller than the width of the central cavity of the housing, so that the sleeve 38 is slidably attached with the inner surface of the continuous wall 18 of the housing unit 12 within the rear-end cavity 30. The sleeve 38 has an outside surface and an inside surface, in which the inside surface has an interior width. The inside surface of the sleeve 38 and the interior surface of the push plate 28 define a hollow shaft. The hollow shaft is in fluid communications with the rear-end cavity 30. The neck 44 is attached to the sleeve 38 of the push plate 28. The neck 44 has a width less than the sleeve 38, so that the neck 44 and the sleeve 38 defining a shoulder 46. When the forward bearing force is exerted on the exterior surface of the push plate 28, then the push plate 28 is capable of sliding forwardly along the inner surface of the continuous wall 18 of the housing unit 12 and the shoulder 46 of the push plate 28 is not capable of sliding past the ledge 42. Whereby the ledge 42 is capable of preventing the push plate 28 from sliding out of the housing 12 and outside of the rear-end cavity 30. The orifice of the ledge 42 is designed to have a width less than the external width of the sleeve 38. When the forward bearing force is exerted on the exterior surface of the push plate 28, then the push plate 28 is capable of sliding forwardly along the inner surface of the continuous wall 18 of the housing unit 12 and the push plate 28 is not capable of sliding past the ledge 42. Whereby the ledge 42 is capable of preventing the push plate 28 from sliding outside of the rear-end cavity 30. The aperture of the rim 50 is designed to have a width less than the external width of the sleeve 38 of the push plate 28, in which the push plate 28 is restrained within the central cavity by the rim 50. The finger protector sheet 36 has a rear surface, a front surface, a hole and an edge. The edge of the finger protector sheet 36 bisects the hollow shaft of the push plate 28 by being attached around a portion of the interior surface of the sleeve 38. The part of the hollow shaft between the finger protector sheet 36 and the interior surface of the push plate 28 defining a top zone of the hollow shaft. The part of the hollow shaft between the finger protection sheet and the remaining part of the hollow shaft define bottom zone of the hollow shaft. The top zone is in fluid communications with the bottom zone through the hole in the finger protector sheet 36. The finger protector sheet 36 is made of a puncture resistant material resistant to being penetrated by the butt-ends of the needles 22. The septum cap 40 is attached to the push plate 28. The spring 48 is attached to ledge 42, so that when the forward bearing force is exerted on the exterior surface of the push plate 28, then the push plate 28 is capable of sliding forwardly along the inner surface of the continuous wall 18 of the housing unit 12. The spring 48 is capable of contacting the push plate 28, in which the spring 48 provides a resistance against the forward bearing force when the push plate 28 slides towards the ledge 42. The second aliquot of the liquid anesthetic agent is affixed within the rear-end cavity 30. The adhesive strip 52 is attached to the rim 50 and is detachably attached to a portion of the exterior surface of the push plate 28. When the forward bearing force is exerted onto the push plate 28, then the adhesive pad is capable of detaching from the push plate 28. The adhesive strip 52 maintains the push plate 28 against the rim 50 until the forward bearing force is exerted onto the push plate 28.

Figure 5:
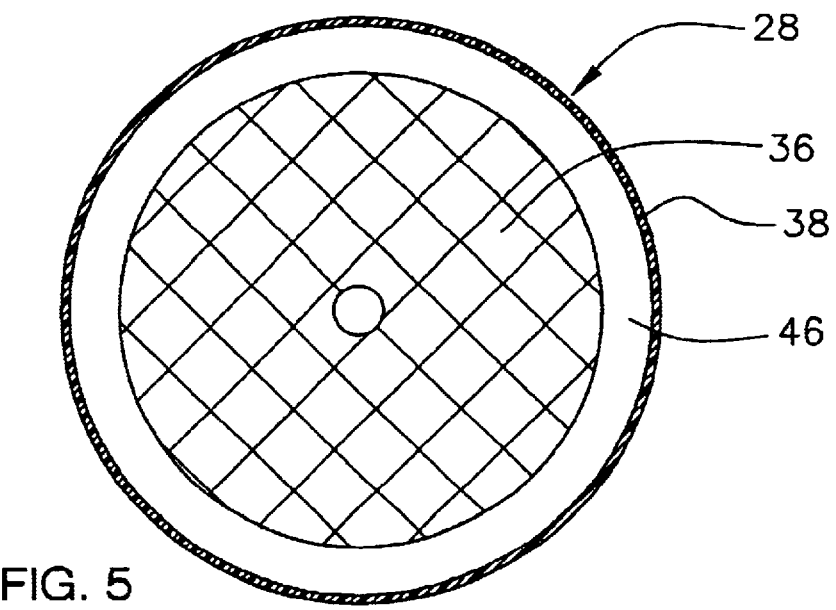
FIG. 5 is a bottom view of bottom view of a push plate of a preferred embodiment of the anesthetic delivery tool of the present invention.

FIG. 5 depicts a bottom view of a push plate 28 of a preferred embodiment of the anesthetic delivery tool 10. The push plate 28 has an exterior surface, an interior surface and an edge. The edge of the push plate 28 is attached around the rear end 14 of the housing. The edge of the push plate 28 comprises a sleeve 38 and a neck 44 (not shown). The sleeve 38 has a exterior width slightly smaller than the width of the central cavity of the housing, so that the sleeve 38 is slidably attached with the inner surface of the continuous wall 18 of the housing unit 12 within the rear-end cavity 30. The neck 44 has a width less than the sleeve 38, so that the neck 44 and the sleeve 38 define a shoulder 46. The finger protector sheet 36 has a rear surface, a front surface, a hole and an edge. The edge of the finger protector sheet 36 is attached around a portion of the interior surface of the sleeve 38 of the push plate 28. The finger protector sheet 36 is made of a puncture resistant material resistant to being penetrated by the blunt-ends of the needles 22.

Figure 6:
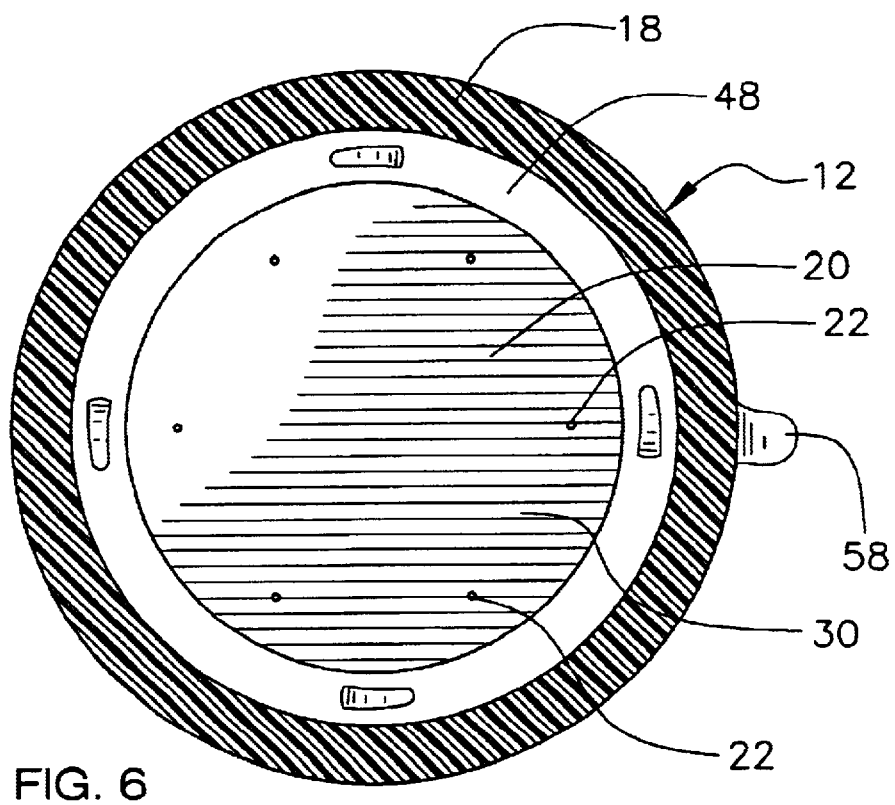
FIG. 6 is a top view of a housing unit of a preferred embodiment of the anesthetic delivery tool of the present invention.

FIG. 6 depicts a top view of a housing unit 12 of a preferred embodiment of the anesthetic delivery tool 10 of the present invention. The housing unit 12 has a continuous wall 18 defining a hollow central cavity with a rear orifice and a front orifice. The continuous wall 18 of the housing unit 12 includes a ledge 42 (not shown) that extends inwardly along a second portion of the interior surface. The ledge 42 defines an orifice having a width. Attached to the ledge 42 is the thin membrane 26 (not shown) and contacting the ledge 42 within the rear-end cavity 30 is the spring 48. The spring 48 provides resistance against to the push plate 28 so that the operator can sense that the injection is complete. Towards the front orifice of the housing unit 12 is the slip plate 20 slidably attached to the hollow central cavity. The plurality of hollow needles 22 is attached longitudinally through the slip plate 20. The butt-ends of the needles 22 are shown extending away from the rear surface of the slip plate 20 and generally pointing towards the rear end 14 of the housing. The thin membrane 26 is penetrateable with the butt-ends of the needles 22 when the forward bearing force is exerted onto the rear surface of the thin membrane 26 which in turn allow the liquid anesthetic stored in the rear end cavity 30 to flow through the needles 22. The pull tab 58 is shown which is attached to the film cover 56 which maintains in place the gel topical anesthetic agent within the front-end cavity.

As to the manner of usage and operation of the present invention, the same should be apparent from the above description. Accordingly, no further discussion relating to the manner of usage and operation will be provided.

While a preferred embodiment of the anesthetic delivery tool has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

With respect to the above description then, it is to be realized that the optimum dimensional relationships for the parts of the invention, to include variations in size materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An anesthetic delivery tool for use in a transmucosal absorption application of a gel topical anesthetic agent and for use in a subdermal injection of a liquid anesthetic agent, said anesthetic delivery tool comprising:

a housing unit having rear end, a front end and a continuous wall defining a hollow central cavity with a rear orifice and a front orifice;

a slip plate having a front surface, a rear surface and an edge, said edge of said slip plate slidably attached around a first portion of said interior surface of said continuous wall of said housing unit, the part of said central cavity between said front surface of said slip plate and the front end of said housing unit defining a front-end cavity, wherein when a forward bearing force is exerted onto said rear surface of said slip plate said slip plate is capable of sliding forward into a portion of said front-end cavity;

a plurality of hollow needles attached longitudinally through said slip plate, said needles having sharp-ends and butt-ends, wherein the sharp-ends of said needles extending away from said front surface of said slip plate into said front-end cavity and generally pointing towards the front end of said housing unit, wherein the butt-ends of said needles extending away from said rear surface of said slip plate and generally pointing towards the rear end of said housing unit, wherein when the forward bearing force is exerted onto said rear surface of said slip plate said slip plate is capable of sliding forward into a portion of said front-end cavity whereby extending said sharp-ends of said needles beyond said front-end cavity;

a first aliquot of the gel topical anesthetic agent affixed onto said front-end cavity, wherein said first aliquot of the gel topical anesthetic agent covering a portion of said sharp-ends of said needles;

a thin membrane having a rear surface, a front surface and an edge, said edge of said thin membrane continuously attached around a second portion of said interior surface of said continuous wall of said housing unit, said thin membrane positioned behind said slip plate, said thin membrane penetrable with said butt-ends of said needles when the forward bearing force is exerted onto said rear surface of said thin membrane;

a push plate having an exterior surface, an interior surface and an edge, said edge of said push plate attached around said rear end of said housing unit, wherein the part of said central cavity between said thin membrane and said push plate defining a rear-end cavity; and an second aliquot of the liquid anesthetic agent affixed within said rear-end cavity.

2. The anesthetic delivery tool described in claim 1, wherein said first portion of the interior surface of said continuous wall of said housing unit defining an inwardly extending ridge, said edge of said slip plate is attached to said ridge, wherein when the forward bearing force is exerted onto said rear surface of said slip plate the attachment of said ridge to said edge of said slip plate is breakable, whereby said slip plate is capable of sliding forward into a portion of said front-end cavity whereby extending said sharp-ends of said needles beyond said front-end cavity.

3. The anesthetic delivery tool described in claim 1, wherein said first portion of the interior surface of said continuous wall of said housing unit defining an inwardly extending lip, said lip positioned near the front end of said housing unit within said central cavity, said lip having a width greater than the width of said slip plate, wherein when the forward bearing force is exerted onto said rear surface of said slip plate, said slip plate is capable of sliding forward into a portion of said front-end cavity and said slip plate is not capable of sliding past said lip, whereby said slip plate is retainable within said front-end cavity of said housing unit.

4. The anesthetic delivery tool described in claim 1 wherein said push plate further comprises a flexible membrane attached around said rear orifice of said housing unit, wherein when said rear-end cavity is filled with liquid anesthetic agent, said push plate is capable of bulging outwardly from said rear-end of said housing unit and when the forward bearing force is exerted onto said exterior surface of said push plate, then said flexible member is capable of bulging inwardly from said rear-end of said housing unit into a portion of said rear-end cavity, whereby reducing the volume in said rear-end cavity.

5. The anesthetic delivery tool described in claim 4 further comprising a finger protector sheet having rear surface, a front surface, a hole and an edge, said edge of said finger protector sheet attached around a portion of said interior surface of said continuous wall of said housing unit said rear-end cavity, wherein said finger protector sheet bisects said rear-end cavity, the part of said rear-end cavity between said finger protector sheet and said push plate defining a top chamber of said rear-end cavity, and the part of said rear-end cavity between said finger protection sheet and said thin membrane defining a bottom chamber of said rear-end cavity, said top chamber in fluid communications with said bottom chamber through said hole in said finger protector sheet, wherein said finger protector sheet is made of a puncture resistant material resistant to being penetrated by said butt-ends of said needles.

6. The anesthetic delivery tool described in claim 1 wherein said edge of said push plate comprises a sleeve having an exterior width slightly smaller than the width of said central cavity of said housing unit, said sleeve slidably attached with said inner surface of said continuous wall of said housing unit within said rear-end cavity, wherein when the forward bearing force is exerted on said exterior surface of said push plate, then said push plate is capable of sliding forwardly along said inner surface of said continuous wall of said housing unit whereby reducing the volume of said rear-end cavity.

7. The anesthetic delivery tool described in claim 6 wherein said sleeve having an outside surface and an inside surface, said inside surface having an interior width, wherein said inside surface of said sleeve and said interior surface of said push plate defining a hollow shaft, said hollow shaft in fluid communications with said rear-end cavity.

8. The anesthetic delivery tool described in claim 7, wherein said push plate further comprising a finger protector sheet having a rear surface, a front surface, a hole and an edge, said edge of said finger protector sheet bisecting said hollow shaft by being attached around a portion of said interior surface of said sleeve wherein the part of said hollow shaft between said finger protector sheet and said interior surface of said push plate defining a top zone of said hollow shaft, and the part of said hollow shaft between said finger protection sheet and the remaining part of said hollow shaft defining a bottom zone of said hollow shaft, said top zone in fluid communications with said bottom zone through said hole in said finger protector sheet, wherein said finger protector sheet is made of a puncture resistant material resistant to being penetrated by said butt-ends of said needles.

9. The anesthetic delivery tool described in claim 8 further comprising a septum cap attached to said push plate, wherein said septum cap intended for allowing the aliquot of liquid anesthetic agent to volumetrically affixed within said rear-end cavity.

10. The anesthetic delivery tool described in claim 9 wherein said second portion so said interior surface of said continuous wall of said housing unit further comprising an inwardly extending ledge, said ledge defining an orifice where said thin membrane is attached, wherein said orifice of said ledge having a width less than the external width of said sleeve, wherein when the forward bearing force is exerted on said exterior surface of said push plate, then said push plate is capable of sliding forwardly along said inner surface of said continuous wall of said housing unit and said push plate is not capable of sliding past said ledge, whereby said ledge is capable of preventing said push plate from sliding outside of said rear-end cavity.

11. The anesthetic delivery tool described in claim 10 further comprising a neck attached to said sleeve of said push plate, said neck having a width less than said sleeve, said neck and said sleeve defining a shoulder, wherein when the forward bearing force is exerted on said exterior surface of said push plate, said push plate is capable of sliding forwardly along said inner surface of said continuous wall of said housing unit and said shoulder of said push plate is not capable of sliding past said ledge, whereby said ledge is capable of preventing said push plate from sliding outside of said rear-end cavity.

12. The anesthetic delivery tool described in claim 10 further comprising a spring attached to ledge, wherein when the forward bearing force is exerted on said exterior surface of said push plate, said push plate is capable of sliding forwardly along said inner surface of said continuous wall of said housing unit and said spring is capable of contacting said push plate, whereby said spring providing resistance against the forward bearing force when said push plate slides towards said ledge.

13. The anesthetic delivery tool described in claim 6 further comprising a rim attached to the rear end of said housing unit, said rim defining an aperture having a width less than the external width of said sleeve of said push plate, wherein said push plate is restrained within said central cavity by said rim.

14. The anesthetic delivery tool described in claim 13 further comprising an adhesive strip attached to said rim and detachably attached to a portion of the exterior surface of said push plate, wherein when the forward bearing force is exerted onto said push plate, said adhesive pad is capable of detaching from said push plate, whereby said adhesive strip maintaining said push plate against said rim until the forward bearing force is exerted onto said push plate.

15. The anesthetic delivery tool described in claim 1 further comprising a gingival adhesive pad attached to said front end of said housing unit, said gingival adhesive pad intended to temporarily attach said housing unit onto a patient's gingival work area.

16. The anesthetic delivery tool described in claim 1 further comprising a detachable film cover attached onto said front end of said housing unit, said film cover maintaining in place said gel topical anesthetic agent within said front-end cavity.

17. The anesthetic delivery tool described in claim 16 wherein said film cover having a pull tab.

18. The anesthetic delivery tool described in claim 1 further comprising a string attached to said housing unit, said string intended to be used as a safety device to retrieve said housing unit from a patients mouth or esophagus.

19. An anesthetic delivery tool for use in a transmucosal absorption application of a gel topical anesthetic agent and for use in a subdermal injection of a liquid anesthetic agent, said anesthetic delivery tool comprising:

a housing unit having rear end, a front end and a continuous wall defining a hollow central cavity with a rear orifice and a front orifice, wherein said continuous wall of said housing unit including:
        a ridge inwardly extending at a first portion of the interior surface of said continuous wall;
        a lip inwardly extending at the front end of said housing unit within said central cavity;
        a ledge inwardly extending along a second portion of said interior surface, said ledge defining an orifice having a width; and a rim attached to the rear end of said housing unit, said rim defining an aperture having a width;

a slip plate having a front surface, a rear surface and an edge, said edge of said slip plate slidably attached around said first portion of said interior surface of said continuous wall of said housing unit, said edge of said slip plate is attached to said ridge, the part of said central cavity between said front surface of said slip plate and the front end of said housing unit defining a front-end cavity, wherein when a forward bearing force is exerted onto said rear surface of said slip plate said slip plate is capable of sliding forward into a portion of said front-end cavity, said lip having a width greater than the width of said slip plate, wherein when the forward bearing force is exerted onto said rear surface of said slip plate, said slip plate is capable of sliding forward into a portion of said front-end cavity and said slip plate is not capable of sliding past said lip, whereby said slip plate is retainable within said front-end cavity of said housing unit;

a plurality of hollow needles attached longitudinally through said slip plate, said needles having sharp-ends and butt-ends, wherein the sharp-ends of said needles extending away from said front surface of said slip plate into said front-end cavity and generally pointing towards the front end of said housing unit, wherein the butt-ends of said needles extending away from said rear surface of said slip plate and generally pointing towards the rear end of said housing unit, wherein when the forward bearing force is exerted onto said rear surface of said slip plate said slip plate is capable of sliding forward into a portion of said front-end cavity whereby extending said sharp-ends of said needles beyond said front-end cavity;

a first aliquot of the gel topical anesthetic agent affixed onto said front-end cavity, wherein said first aliquot of the gel topical anesthetic agent covering a portion of said sharp-ends of said needles;

a thin membrane having a rear surface, a front surface and an edge, said edge of said thin membrane continuously attached around said ledge at said second portion of said interior surface of said continuous wall of said housing unit, said thin membrane positioned behind said slip plate, said thin membrane penetrable with said butt-ends of said needles when the forward bearing force is exerted onto said rear surface of said thin membrane;

a push plate having an exterior surface, an interior surface and an edge, said edge of said push plate attached around said rear end of said housing unit, wherein the part of said central cavity between said thin membrane and said push plate defining a rear-end cavity, said edge of said push plate comprises a sleeve and a neck, said sleeve having an exterior width slightly smaller than the width of said central cavity of said housing unit, said sleeve slidably attached with said inner surface of said continuous wall of said housing unit within said rear-end cavity, said sleeve having an outside surface and an inside surface, said inside surface having an interior width, wherein said inside surface of said sleeve and said interior surface of said push plate defining a hollow shaft, said hollow shaft in fluid communications with said rear-end cavity, said neck attached to said sleeve of said push plate, said neck having a width less than said sleeve, said neck and said sleeve defining a shoulder, wherein when the forward bearing force is exerted on said exterior surface of said push plate, said push plate is capable of sliding forwardly along said inner surface of said continuous wall of said housing unit and said shoulder of said push plate is not capable of sliding past said ledge, whereby said ledge is capable of preventing said push plate from sliding outside of said rear-end cavity, said orifice of said ledge having a width less than the external width of said sleeve, wherein when the forward bearing force is exerted on said exterior surface of said push plate, then said push plate is capable of sliding forwardly along said inner surface of said continuous wall of said housing unit and said push plate is not capable of sliding past said ledge, whereby said ledge is capable of preventing said push plate from sliding outside of said rear-end cavity, said aperture of said rim having a width less than the external width of said sleeve of said push plate, whereby said push plate is restrained within said central cavity by said rim;

a finger protector sheet having a rear surface, a front surface, a hole and an edge, said edge of said finger protector sheet bisecting said hollow shaft of said push plate by being attached around a portion of said interior surface of said sleeve wherein the part of said hollow shaft between said finger protector sheet and said interior surface of said push plate defining a top zone of said hollow shaft, and the part of said hollow shaft between said finger protection sheet and the remaining part of said hollow shaft defining a bottom zone of said hollow shaft, said top zone in fluid communications with said bottom zone through said hole in said finger protector sheet, wherein said finger protector sheet is made of a puncture resistant material resistant to being penetrated by said butt-ends of said needles;

a septum cap attached to said push plate;

a spring attached to ledge, wherein when the forward bearing force is exerted on said exterior surface of said push plate, said push plate is capable of sliding forwardly along said inner surface of said continuous wall of said housing unit and said spring is capable of contacting said push plate, whereby said spring providing resistance against the forward bearing force when said push plate slides towards said ledge;

an second aliquot of the liquid anesthetic agent affixed within said rear-end cavity;

an adhesive strip attached to said rim and detachably attached to a portion of the exterior surface of said push plate, wherein when the forward bearing force is exerted onto said push plate, said adhesive pad is capable of detaching from said push plate, whereby said adhesive strip maintaining said push plate against said rim until the forward bearing force is exerted onto said push plate;

a gingival adhesive pad attached to said front end of said housing unit, said gingival adhesive pad intended to temporarily attach said housing unit onto a patient's gingival work area;

a detachable film cover attached onto said front end of said housing unit, said film cover maintaining in place said gel topical anesthetic agent within said front-end cavity, said film cover having a pull tab; and a string attached to said housing unit.

20. A method of using an anesthetic delivery tool for use in a transmucosal absorption application of a gel topical anesthetic agent and for use in a subdermal injection of a liquid anesthetic agent, said method comprising the steps of:

obtaining the dental anesthetic delivery tool comprising:

a housing unit having rear end, a front end and a continuous wall defining a hollow central cavity with a rear orifice and a front orifice, wherein the continuous wall of the housing unit including:

a ridge inwardly extending at a first portion of the interior surface of the continuous wall;

a lip inwardly extending at the front end of the housing unit within the central cavity;

a ledge inwardly extending along a second portion of the interior surface, the ledge defining an orifice having a width; and a rim attached to the rear end of the housing unit, the rim defining an aperture having a width;

a slip plate having a front surface, a rear surface and an edge, the edge of the slip plate slidably attached around the first portion of the interior surface of the continuous wall of the housing unit, the edge of the slip plate is attached to the ridge, the part of the central cavity between the front surface of the slip plate and the front end of the housing unit defining a front-end cavity, wherein when a forward bearing force is exerted onto the rear surface of the slip plate the slip plate is capable of sliding forward into a portion of the front-end cavity, the lip having a width greater than the width of the slip plate, wherein when the forward bearing force is exerted onto the rear surface of the slip plate, the slip plate is capable of sliding forward into a portion of the front-end cavity and the slip plate is not capable of sliding past the lip, whereby the slip plate is retainable within the front-end cavity of the housing unit;

a plurality of hollow needles attached longitudinally through the slip plate, the needles having sharp-ends and butt-ends, wherein the sharp-ends of the needles extending away from the front surface of the slip plate into the front-end cavity and generally pointing towards the front end of the housing unit, wherein the butt-ends of the needles extending away from the rear surface of the slip plate and generally pointing towards the rear end of the housing unit, wherein when the forward bearing force is exerted onto the rear surface of the slip plate the slip plate is capable of sliding forward into a portion of the front-end cavity whereby extending the sharp-ends of the needles beyond the front-end cavity;

a first aliquot of the gel topical anesthetic agent affixed onto the front-end cavity, wherein the first aliquot of the gel topical anesthetic agent covering a portion of the sharp-ends of the needles;

a thin membrane having a rear surface, a front surface and an edge, the edge of the thin membrane continuously attached around the ledge at the second portion of the interior surface of the continuous wall of the housing unit, the thin membrane positioned behind the slip plate, the thin membrane penetrable with the butt-ends of the needles when the forward bearing force is exerted onto the rear surface of the thin membrane;

a push plate having an exterior surface, an interior surface and an edge, the edge of the push plate attached around the rear end of the housing unit, wherein the part of the central cavity between the thin membrane and the push plate defining a rear-end cavity, the edge of the push plate comprises a sleeve and a neck, the sleeve having an exterior width slightly smaller than the width of the central cavity of the housing unit, the sleeve slidably attached with the inner surface of the continuous wall of the housing unit within the rear-end cavity, the sleeve having an outside surface and an inside surface, the inside surface having an interior width, wherein the inside surface of the sleeve and the interior surface of the push plate defining a hollow shaft, the hollow shaft in fluid communications with the rear-end cavity, the neck attached to the sleeve of the push plate, the neck having a width less than the sleeve, the neck and the sleeve defining a shoulder, wherein when the forward bearing force is exerted on the exterior surface of the push plate, the push plate is capable of sliding forwardly along the inner surface of the continuous wall of the housing unit and the shoulder of the push plate is not capable of sliding past the ledge, whereby the ledge is capable of preventing the push plate from sliding outside of the rear-end cavity, the orifice of the ledge having a width less than the external width of the sleeve, wherein when the forward bearing force is exerted on the exterior surface of the push plate, then the push plate is capable of sliding forwardly along the inner surface of the continuous wall of the housing unit and the push plate is not capable of sliding past the ledge, whereby the ledge is capable of preventing the push plate from sliding outside of the rear-end cavity, the aperture of the rim having a width less than the external width of the sleeve of the push plate, whereby the push plate is restrained within the central cavity by the rim;

a finger protector sheet having a rear surface, a front surface, a hole and an edge, the edge of the finger protector sheet bisecting the hollow shaft of the push plate by being attached around a portion of the interior surface of the sleeve wherein the part of the hollow shaft between the finger protector sheet and the interior surface of the push plate defining a top zone of the hollow shaft, and the part of the hollow shaft between the finger protection sheet and the remaining part of the hollow shaft defining a bottom zone of the hollow shaft, the top zone in fluid communications with the bottom zone through the hole in the finger protector sheet, wherein the finger protector sheet is made of a puncture resistant material resistant to being penetrated by the butt-ends of the needles;

a septum cap attached to the push plate;

a spring attached to ledge, wherein when the forward bearing force is exerted on the exterior surface of the push plate, the the push plate is capable of sliding forwardly along the inner surface of the continuous wall of the housing unit and the spring is capable of contacting the push plate, whereby the spring providing resistance against the forward bearing force when the push plate slides towards the ledge;

an second aliquot of the liquid anesthetic agent affixed within the rear-end cavity;

an adhesive strip attached to the rim and detachably attached to a portion of the exterior surface of the push plate, wherein when the forward bearing force is exerted onto the push plate, the adhesive pad is capable of detaching from the push plate, whereby the adhesive strip maintaining the push plate against the rim until the forward bearing force is exerted onto the push plate;

a gingival adhesive pad attached to the front end of the housing unit, the gingival adhesive pad intended to temporarily attach the housing unit onto a patient's gingival work area;

a detachable film cover attached onto the front end of the housing unit, the film cover maintaining in place the gel topical anesthetic agent within the front-end cavity, the film cover having a pull tab; and a string attached to the housing unit;

identifying the gingival work area in the patient's mouth;

removing the detachable film cover from the front end of the housing unit;

adhering the front end of the housing unit to the gingival work area in the patient's mouth;

aligning the string outside of the patient's mouth;

allowing time to pass so that the gel topical anesthetic agent can be transmucosally absorbed in the gingival work area in the patient's mouth;

positioning a finger over the exterior surface of the push plate;

exerting the forward bearing force onto the exterior surface of the push plate so that the slip plate slides forward and the sharp-ends of the needles puncture the gingival work area in the patient's mouth as well as penetrate the thin membrane and subsequently inject the liquid anesthetic agent into the surrounding tissue of the gingival work area in the patient's mouth;

removing the finger from the exterior surface of the push plate;

pulling the housing unit out of the patients mouth; and discarding the used housing unit.

\* \* \* \* \*